(12) United States Patent
Evron

(10) Patent No.: US 7,894,570 B2
(45) Date of Patent: Feb. 22, 2011

(54) AUTOMATIC DOSE ADAPTATION AS A FUNCTION OF PATIENT BODY MASS INDEX IN CT CALCIUM SCORING

(75) Inventor: Rami Evron, Tel-Aviv (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1308 days.

(21) Appl. No.: 10/595,989

(22) PCT Filed: Nov. 16, 2004

(86) PCT No.: PCT/IB2004/052453

§ 371 (c)(1),
(2), (4) Date: May 24, 2006

(87) PCT Pub. No.: WO2005/051198

PCT Pub. Date: Jun. 9, 2005

(65) Prior Publication Data

US 2007/0081630 A1    Apr. 12, 2007

Related U.S. Application Data

(60) Provisional application No. 60/524,955, filed on Nov. 25, 2003.

(51) Int. Cl.
G01N 23/00    (2006.01)
(52) U.S. Cl. .............................. 378/8; 378/95; 378/108; 378/109; 378/110
(58) Field of Classification Search ...................... 378/8, 378/95, 108, 109, 110
See application file for complete search history.

(56) References Cited

U.S. PATENT DOCUMENTS

| | | | | |
|---|---|---|---|---|
| 4,597,094 A | * | 6/1986 | Kleinman | 378/95 |
| 4,922,915 A | * | 5/1990 | Arnold et al. | 382/128 |
| 5,349,625 A | * | 9/1994 | Born et al. | 378/95 |
| 5,696,807 A | * | 12/1997 | Hsieh | 378/109 |
| 5,949,811 A |   | 9/1999 | Baba et al. | |

(Continued)

FOREIGN PATENT DOCUMENTS

EP    1 354 554 A2    10/2003

(Continued)

OTHER PUBLICATIONS

Coppenrath, E., et al.; Spiral CT of the abdomen: weight-adjusted dose reduction; 2001; Fortschr Rontgenstr; 173:52-56.

(Continued)

Primary Examiner—Hoon Song
Assistant Examiner—Mona M Sanei

(57) ABSTRACT

A weight (22) and height (24) of a patient who is to undergo a calcium screening examination in an x-ray diagnostic scanner (10) is used to calculate an appropriate x-ray dose in terms of tube current (mAs) for the calcium screening examination in accordance with the formula: $mAs=c(BMI)^2$, where BMI is a patient's body mass index defined as: $BMI=$patent weight$\_$(patient height)$^2$ and C is a constant selected in accordance with a target required noise. In this manner, patients can be scanned with a minimum dose necessary to achieve the target noise, e.g., 20 HU. The images can be compared with earlier (and subsequent) images that have the same target noise.

19 Claims, 2 Drawing Sheets

U.S. PATENT DOCUMENTS

Figure 1:
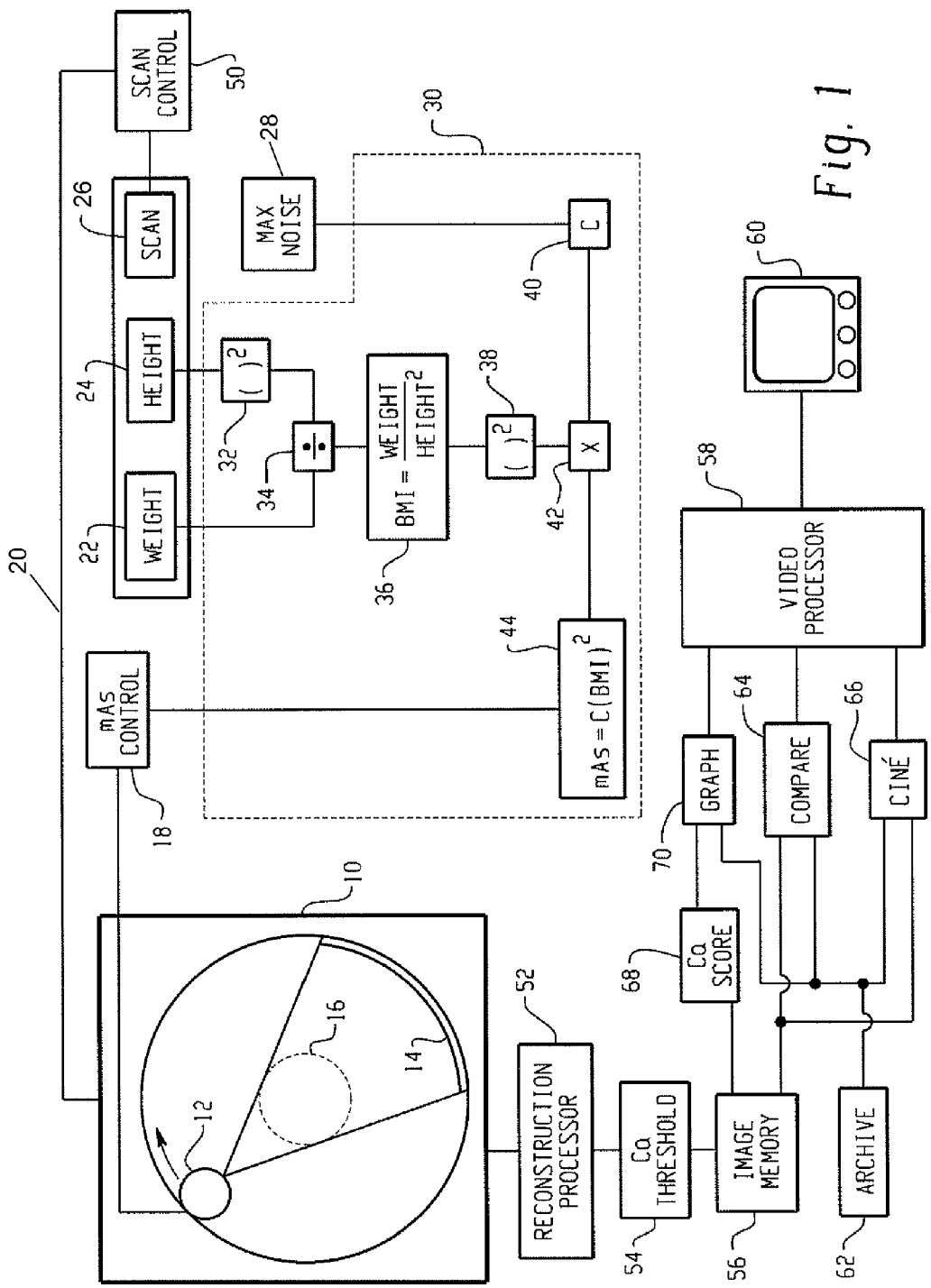

| | | | |
|---|---|---|---|
| 6,233,304 B1* | 5/2001 | Hu et al. | 378/8 |
| 6,385,280 B1 | 5/2002 | Bittl et al. | |
| 7,116,756 B2* | 10/2006 | Klingenbeck-Regn et al. | 378/95 |
| 7,636,422 B2* | 12/2009 | Jianying | 378/110 |
| 2003/0097062 A1* | 5/2003 | Toth et al. | 600/425 |
| 2005/0031080 A1 | 2/2005 | Klingenbeck-Regen et al. | |

FOREIGN PATENT DOCUMENTS

| | | |
|---|---|---|
| WO | WO 03/022018 A1 | 3/2003 |

OTHER PUBLICATIONS

Hong, C., et al.; Coronary Artery Calcium Measurement with Multi-Detector Row CT: In Vitro Assessment of Effect of Radiation Dose; 2002; Radiology; 225(3)901-906.

Jung, B., et al.; Individually weight-adapted examination protocol in retrospectively ECG-gated MSCT of the heart; 2003; Eur Radiol; 13:2560-2566.

Mahnken, A.H., et al.; Detection of Colonary Calcifications: Feasibility of Dose Reduction with a Body Weight-Adapted Examination Protocol; 2003; AJR;181:533-538.

Sevrukov, A., et al.; Electron Beam Tomography Imaging of Coronary Calcium: The Effect of Body Mass Index on Radiologic Noise; 2002; J. Comp. Assist. Tomog.; 26(4)592-597.

Starck, G., et al.; A method to obtain the same levels of CT image noise for patients of various sizes, to minimize radiation dose; 2002; B. J. of Radiology; 75:140-150.

Tack, D., et al.; Dose Reduction in Multidetector CT Using Attenuation-Based Online Tube Current Modulation; 2003; AJR; 181:331-334.

Wildberger, J.E., et al.; Individually Adapted Examination Protocols for Reduction of Radiation Exposure in Chest CT; 2001; Investigative Radiology; 36(10)604-611.

* cited by examiner

AUTOMATIC DOSE ADAPTATION AS A FUNCTION OF PATIENT BODY MASS INDEX IN CT CALCIUM SCORING

CROSS REFERENCE TO RELATED APPLICATIONS

This application claims the benefit of U.S. provisional application Ser. No. 60/524,955 filed Nov. 25, 2003, which is incorporated herein by reference.

The present invention relates to the diagnostic imaging arts. It finds particular application in conjunction with calcium scoring with CT scanners and will be described with particular reference thereto.

The presence of calcium deposits in the coronary arteries has been recognized as a marker for atherosclerotic coronary artery disease. Patients who are at risk are screened for calcium in order to follow the calcium build up rate and to assess the influence of certain medication on this rate. Each screening generates a diagnostic image in which tissue above a preselected threshold, e.g., 130 HU, is assumed to be calcium and is marked with a differentiating color to develop a calcium score. The images are compared with images from previous examinations to determine the change in the calcium deposits with time.

Repeated calcium scoring examinations can deliver a substantial cumulative amount of ionizing radiation. Exposure to radiation is a concern, especially in subjects in the screening population. Although the CT radiation dose may be relatively low per subject per scan, the added risk to the population is substantive, with unknown long-term effects. Accordingly, attempts have been made to reduce the radiation dose.

Calcium scanning has been conducted with an arbitrarily selected fixed low dose, such as driving the x-ray tube with 40 mAs or other fixed small tube currents. While the calcium scoring examinations have, for some patients, been excellent at low doses, the examinations for other patients have had unacceptably high noise. High noise causes numerous voxels of the reconstructed image to have a noise influenced Hounsfield unit (HU) level. Because noise is additive (subtractive) to the Hounsfield value of each pixel, noise can cause voxels below the threshold to be raised above the threshold and appear as calcium. In other instances, random noise appearing in a voxel corresponding to calcium can drive the HU value of the voxel below the calcium threshold. By consensus, it has been decided that 20 HU of noise is the required noise for acceptable calcium scoring examinations.

It has been found that in low dose (low mAs) diagnostic images, good noise statistics are achieved for subjects with a relatively small lateral thickness and high noise statistics occur for patients with a larger lateral thickness. It has been proposed that patients be divided into three size categories: small (less than 32 cm lateral thickness), medium (32-38 cm lateral thickness), and large (over 38 cm lateral thickness). The proposal calls for manufacturers of CT scanners to set a recommended dose (mAs) for patients in each size range. Although this solution has advantages, it still irradiates patients below the upper thickness end of the two thinner ranges with more radiation than necessary. Moreover, it may not radiate patients significantly over 38 cm in lateral thickness with a high enough dose to achieve the 20 HU maximum noise level standard.

The present invention provides a new and improved solution which overcomes the above-referenced problems and others.

In accordance with one aspect of the present invention, a diagnostic imaging device is provided. An x-ray tube irradiates a patient with an x-ray beam. A dose controller controls milliamperes of an x-ray tube current to control radiation dose. A dose processor calculates a target maximum patient dose in accordance with physical parameters of the patient to be examined.

In accordance with another aspect of the present invention, a method of diagnostic imaging is provided. A radiation dose of an x-ray tube is selected in accordance with physical parameters of a patient to be examined. An x-ray diagnostic examination of the patient is performed with an x-ray beam with the selected radiation dose.

In accordance with a more limited aspect of the present invention, the maximum target radiation dose is achieved with an x-ray tube current (mAs) that is proportional to the patient's body mass index (BMI) squared.

One advantage of the present invention is that it minimizes radiation dose, while still maintaining noise levels below a preselected threshold.

Another advantage of this invention resides in its simplicity and ease of implementation.

Another advantage resides in maintaining a consistent noise level over a series of images acquired over a long period (years).

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
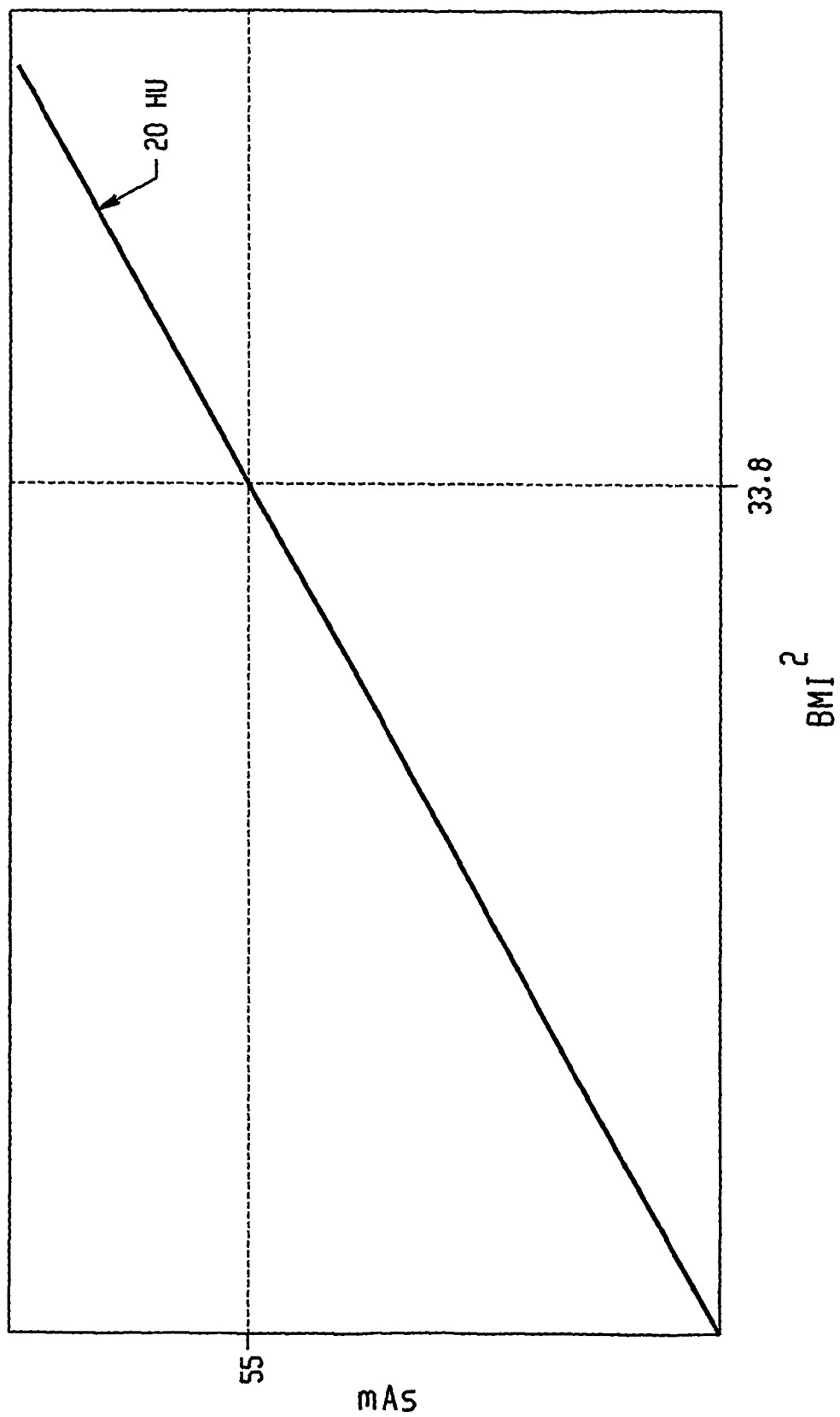

FIG. 1 is a diagrammatic illustration of a diagnostic imaging system in accordance with the present invention; and, FIG. 2 is a graphical illustration of the relationship between the mAs and the body mass index at the selected noise level of 20 HU.

A CT scanner 10 includes an x-ray tube 12 which generates a beam of radiation, such as a fan-beam or cone-beam. The radiation is received by a detector array 14 disposed across an examination region 16 from the x-ray source to receive radiation that has passed through a portion of a subject in the examination region. An x-ray controller 18 controls the milliamperes (mAs) values of the x-ray tube which, in turn, adjusts the dose of radiation delivered to the subject in the examination region 16.

A user input device 20 includes a means 22 for inputting the patient's weight, a means 24 for inputting the patient's height, and a means 26 for inputting other selected scan control parameters and information, as are conventional in the art. These inputting means typically include a keyboard, number pad, touch screen, or the like. A target required noise memory 28 stores the target required noise level. In the preferred embodiment, the target required noise level is a preselected standard which remains fixed, but which may be changed if the standard changes. Alternately, the required noise can be designated through the user input means to enable the clinician to select a different target noise level.

A dose selection processor 30 includes an algorithm or means 32 for squaring the patient's height and an algorithm or means 34 for dividing the patient's weight by the square of the patient's height to generate the body mass index (BMI) which is defined as being the patient's weight divided by the square of his height. The body mass index is stored in a buffer 36. An algorithm or means 38 squares the body mass index. The target required noise from the required noise memory 28 accesses a look-up table 40 to retrieve a corresponding constant. In the preferred embodiment in which the weight is entered in kilograms, the height in meters, and the target required noise is 20 HU, an appropriate constant is 0.05. A multiplying algorithm or means 42 multiplies the square of the body mass index by the constant which generates the mAs value, which may be stored in a corresponding buffer 44. The calculated mAs value is communicated to the dose controller 18 which controls the x-ray tube to generate a tube current with the calculated level of milliamperes (mAs).

FIG. 2 is a graphical illustration of the relationship between the mAs and the body mass index squared at the selected noise level of 20 HU. It will be noted that this relationship is a linear relationship with a slope equal to the constant for the selected noise level. For a target maximum noise of 20 HU, the slope of the linear relationship is 0.05. For lower noise, the slope is steeper, and for higher noise, the slope is more shallow.

Once the dose level has been set, the user input device 20 enables a scan controller 50 to initiate a CT scan. As the radiation source 12 is rotated around the examination region, a reconstruction processor 52 reconstructs the image data from the detector 14 into a diagnostic image representation. A thresholding means or algorithm 54 thresholds the resultant diagnostic image to differentiate calcium from other tissue, e.g., at 130 HU. The thresholded, calcium-enhanced image representation is stored in an image memory 56. A video processor 58 withdraws selected portions of the calcium-enhanced image representation for display on a monitor 60. Preferably, one or more prior calcium scans of the same subject are retrieved from an archive 62. A comparing algorithm or means 64 compares the most recent calcium scan image representation from the memory 56 with the archived image representations. The video processor may then convey a difference image between the most recent calcium scan image representation and a selected prior calcium scan representation to the monitor to generate a display indicative of the change in calcium between the two scans. Optionally, a cine image processor 66 displays the historical and new image sequentially in a cine mode. A calcium score calculator 68 calculates the calcium score from the current image. A graphing means or processor 70 compares a plurality of calcium scores, including the current calcium score and others from the archive to generate a graphical display indicative of calcium build-up.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An x-ray diagnostic imaging device including:
    an x-ray tube for irradiating a patient with an x-ray beam;
    a dose controller for controlling milliamperes (mAs) of an x-ray tube current to control radiation dose; and
    a dose selection processor for calculating a target maximum patient dose based on $C(\text{patient weight} \div (\text{patient height})^2)^2$, wherein C is a constant determined based on a target required noise level.

2. The device according to claim 1, further including a user input means for inputting the patient's height and weight.

3. The device according to claim 2, wherein the dose selection processor is connected with the user input means to receive the input weight and height therefrom, the dose selection processor including:
    a means for squaring the patient's height;
    a means for dividing the patient's weight squared by the patient's height squared to calculate a body mass index of the patient;
    a means for squaring the body mass index; and
    a means for multiplying the body mass index squared by the constant.

4. The device according to claim 3, further including:
    a target required noise memory for storing the target required noise level; and
    a means for converting the target required noise level into the constant.

5. The device according to claim 1, wherein the dose selection processor controls the dose controller control the tube to produce a tube current which is proportional to the examined patient's body mass index squared.

6. The device according to claim 5, further including:
    a reconstruction processor for reconstructing examination data from the x-ray diagnostic imaging device into an image representation;
    a thresholding means for thresholding the image representation for calcium to generate a calcium enhanced image representation;
    a means for storing the calcium enhanced image representation; and
    a means for displaying the calcium enhanced image representation.

7. A method of diagnostic imaging including:
    selecting a target required radiation dose of an x-ray tube in accordance with physical parameters of a patient to be examined, wherein the target required radiation dose is determined based on a body mass index for the patient and a constant selected in accordance with a targeted noise level; and
    performing an x-ray diagnostic examination of the patient with an x-ray beam with the selected radiation dose.

8. The method according to claim 7, wherein selecting the radiation dose includes:
    calculating a tube current in milliamperes which is proportional to the body mass index squared of the patient to be examined.

9. The method according to claim 7, wherein the patient physical parameters include:
    a weight and height of the examined patient.

10. The method according to claim 9, further including:
    squaring the patient's height;
    dividing the patient's weight by the patient's height squared to generate the body mass index;
    squaring the body mass index; and
    multiplying the body mass index squared by the constant to calculate a tube current for the x-ray tube.

11. The method according to claim 7, wherein the targeted noise level is 20 HU and the constant is 0.05.

12. The method according to claim 7, further including:
    setting a tube current of the x-ray tube to the product of the body mass index squared and the constant.

13. The method according to claim 7, wherein the patient parameters include a patient body mass index.

14. The method according to claim 13, wherein the x-ray tube dose in milliamperes of tube current is selected to be proportional to the body mass index squared.

15. The method according to claim 14, further including:
    reconstructing an image representation from data generated while performing a diagnostic examination; and
    thresholding the reconstructed image representation with a calcium threshold to generate a calcium-enhanced diagnostic image representation.

16. The method according to claim 15, further including:

comparing the calcium-enhanced image representation with prior calcium-enhanced image representations of the same patient.

17. The method according to claim 16, wherein a target noise level of the present calcium-enhanced image representation is the same as a noise level of the prior calcium-enhanced image representations.

18. A method, comprising:

obtaining patient physical parameters, including the patient's weight and height;

squaring the patient's height;

dividing the patient's weight by the patient's height squared to generate a body mass index;

squaring the body mass index;

multiplying the body mass index squared by a constant to calculate a tube current for the x-ray tube, wherein the constant is selected in accordance with a noise level;

selecting a radiation dose of an x-ray tube in accordance with the calculated tube current; and performing an x-ray diagnostic examination of the patient with an x-ray beam based on the selected radiation dose.

19. The method of claim 18, wherein the noise level represents a target required noise level.

* * * * *